(12) United States Patent
Portal et al.

(10) Patent No.: US 12,257,336 B2
(45) Date of Patent: Mar. 25, 2025

(54) COSMETIC COMPOSITION COMPRISING A POLYHYDROXYALKANOATE IN AN OILY MEDIUM

(71) Applicant: L'OREAL, Paris (FR)

(72) Inventors: Julien Portal, Aulnay-sous-Bois (FR); Romain Garcon, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 889 days.

(21) Appl. No.: 17/291,717

(22) PCT Filed: Dec. 20, 2019

(86) PCT No.: PCT/EP2019/086809
§ 371 (c)(1),
(2) Date: May 6, 2021

(87) PCT Pub. No.: WO2020/128050
PCT Pub. Date: Jun. 25, 2020

(65) Prior Publication Data
US 2022/0008317 A1    Jan. 13, 2022

(30) Foreign Application Priority Data
Dec. 20, 2018   (FR) ...................................... 1873652

(51) Int. Cl.
| | |
|---|---|
| *A61K 8/85* | (2006.01) |
| *A61K 8/34* | (2006.01) |
| *A61K 8/92* | (2006.01) |
| *A61Q 1/06* | (2006.01) |
| *A61Q 1/10* | (2006.01) |

(52) U.S. Cl.
CPC .................. *A61K 8/85* (2013.01); *A61K 8/34* (2013.01); *A61K 8/922* (2013.01); *A61Q 1/06* (2013.01); *A61Q 1/10* (2013.01); *A61K 2800/34* (2013.01); *A61K 2800/591* (2013.01); *A61K 2800/85* (2013.01)

(58) Field of Classification Search
CPC ............................. A61K 8/85; A61K 2800/85
See application file for complete search history.

(56) References Cited

U.S. PATENT DOCUMENTS 10,113,060 B2 * 10/2018 Krishnaswamy ....... C08L 67/04
2018/0265663 A1 * 9/2018 Kuwagaki ................ A61Q 1/02

FOREIGN PATENT DOCUMENTS

| EP | 1 980 235 A1 | 10/2008 | |
|---|---|---|---|
| JP | 2009-171883 A | 8/2009 | |
| WO | WO 2015/123049 A1 | 8/2015 | |
| WO | WO-2018178899 A1 * | 10/2018 | ............. A61K 8/025 |

* cited by examiner

Primary Examiner — Andrew S Rosenthal
(74) Attorney, Agent, or Firm — POLSINELLI PC

(57) ABSTRACT

The invention relates to a composition comprising: a) a polyhydroxyalkanoate copolymer comprising the following polymeric units A, B and C: —[—O—CH(R1)—CH$_2$—CO—]-unit A —[—O—CH(R2)—CH$_2$—CO—]-unit B —[—O—CH(R3)—CH$_2$—CO—]-unit C in which: R1 denotes a linear alkyl radical having from 5 to 9 carbon atoms; R2 denotes a linear alkyl radical having a carbon number corresponding to the number of carbon atoms of the R1 radical −2; R3 denotes a linear alkyl radical having a carbon number corresponding to the number of carbon atoms of the R1 radical −4; b) an oily medium comprising a non-silicone oil chosen from ester oils, carbonate oils and nonpolar hydrocarbon oils having from 8 to 14 carbon atoms.

21 Claims, No Drawings

COSMETIC COMPOSITION COMPRISING A POLYHYDROXYALKANOATE IN AN OILY MEDIUM

CROSS REFERENCE TO RELATED APPLICATIONS

This application is a National Phase filing under 35 U.S.C. § 371 of PCT/EP2019/086809 filed on 20 Dec. 2019; which application in turn claims priority to Application No. 1873652 filed in France on 20 Dec. 2018. The entire contents of each application are hereby incorporated by reference.

The present invention relates to a cosmetic composition comprising a polyhydroxyalkanoate in an oily medium, as well as to a method for the treatment of keratinous substances employing such a composition.

It is known to use, in cosmetics, film-forming polymers which can be transported in organic media, such as hydrocarbon oils. Polymers are used in particular as film-forming agent in makeup products, such as mascaras, eyeliners, eye shadows or lipsticks.

The document FR-A-2964663 describes a cosmetic composition comprising pigments coated with a $C_3$-$C_{21}$ polyhydroxyalkanoate, such as poly(hydroxybutyrate-co-hydroxyvalerate).

The document WO2011/154508 describes a cosmetic composition comprising a 4-carboxy-2-pyrrolidinone ester derivative and a film-forming polymer which can be a polyhydroxyalkanoate, such as polyhydroxybutyrate, polyhydroxyvalerate and polyhydroxybutyrate-co-polyhydroxyvalerate.

The document US-A-2015/274972 describes a cosmetic composition comprising a cosmetic composition comprising a thermoplastic resin, such as a polyhydroxyalkanoate, in aqueous dispersion and a silicone elastomer.

The document WO 2018/17899 discloses a cosmetic composition comprising a polyhydroxyalkanoate (PHA) in the form of solid particles and an oily phase. PHA is used to absorb oily substance in order to obtain a "soft focus" effect on skin.

A need thus exists to have available a composition comprising a solubilized polyhydroxyalkanoate making it possible to obtain a film exhibiting good cosmetic properties, in particular good resistance to oils and to sebum, as well as a good mattness.

The applicant company has discovered that specific polyhydroxyalkanoate copolymers, as defined below, can be easily employed in the oily media specially selected, thus making it possible to obtain homogeneous compositions because of the good solubilization of the copolymer in the oily medium. The composition exhibits good stability, in particular after storage for one month at ambient temperature (25° C.). The composition, in particular after its application to keratinous substances, makes it possible to obtain a film having good cosmetic properties, in particular good resistance to oils and to sebum, as well as a matt appearance.

A subject matter of the present invention is thus a composition comprising:

a) a polyhydroxyalkanoate copolymer comprising, preferably consisting of, the following polymeric units A, B and C:

—[—O—CH(R1)-CH$_2$—CO—]— unit A

—[—O—CH(R2)-CH$_2$—CO—]— unit B

—[—O—CH(R3)-CH$_2$—CO—]— unit C in which:
R1 denotes a linear alkyl radical having from 5 to 9 carbon atoms;
R2 denotes a linear alkyl radical having a carbon number corresponding to the number of carbon atoms of the R1 radical −2;
R3 denotes a linear alkyl radical having a carbon number corresponding to the number of carbon atoms of the R1 radical −4;
the molar percentage of unit A being greater than the molar percentage of unit B and greater than the molar percentage of unit C;

b) an oily medium comprising a non-silicone oil chosen from:
ester oils, carbonate oils,
branched nonpolar hydrocarbon oils having from 8 to 14 carbon atoms, as a mixture with a monoalcohol having from 2 to 6 carbon atoms according to a monoalcohol/branched nonpolar hydrocarbon oil ratio by weight ranging from 1/99 to 10/90; and
when the polymer is such that the R1 alkyl group comprises from 6 to 9 carbon atoms, the non-silicone oil is also chosen from nonpolar hydrocarbon oils having from 8 to 14 carbon atoms in the absence of monoalcohol having from 2 to 6 carbon atoms;
when the polymer is such that the R1 alkyl group comprises 9 carbon atoms, the non-silicone oil is also chosen from hydrogenated polyisobutylenes.

Another subject matter of the invention is a nontherapeutic cosmetic method for the treatment of keratinous substances, comprising the application, to the keratinous substances, of a composition as defined above. The treatment method is in particular a method for caring for or making up keratinous substances.

The polyhydroxyalkanoate copolymer of the composition according to the invention comprises the units A, B and C as defined above.

Preferably, in the copolymer, the unit A is present in a molar percentage ranging from 40% to 97.5%, the unit B is present in a molar percentage ranging from 2% to 40% and the unit C is present in a molar percentage ranging from 0.5% to 20%, with respect to all of the units A, B and C.

According to a first embodiment of the composition according to the invention, the copolymer comprises units A having an R1 alkyl radical comprising 5 carbon atoms, units B having an alkyl radical having 3 carbon atoms and units C having an alkyl radical having 1 carbon atom. Advantageously, the copolymer comprises from 85 mol % to 97.5 mol % of unit A, from 2 mol % to 10 mol % of unit B and from 0.5 mol % to 7 mol % of unit C.

According to a second embodiment of the composition according to the invention, the copolymer comprises units A having an R1 alkyl radical comprising 6 carbon atoms, units B having an alkyl radical having 4 carbon atoms and units C having an alkyl radical having 2 carbon atoms. Advantageously, the copolymer comprises from 60 mol % to 94.5 mol % of unit A, from 5 mol % to 35 mol % of unit B and from 0.5 mol % to 7 mol % of unit C.

According to a third embodiment of the composition according to the invention, the copolymer comprises units A having an R1 alkyl radical comprising 9 carbon atoms, units B having an alkyl radical having 7 carbon atoms and units C having an alkyl radical having 5 carbon atoms. Advantageously, the copolymer comprises from 40 mol % to 50 mol % of unit A, from 30 mol % to 40 mol % of unit B and from 10 mol % to 20 mol % of unit C.

The copolymer preferably has a number-average molecular weight ranging from 50 000 to 150 000.

The molecular weight can be measured in particular by size exclusion chromatography. A method is described below in the examples.

The copolymer can be present in the composition according to the invention in a content ranging from 0.1% to 30% by weight, with respect to the total weight of the composition, preferably ranging from 0.1% to 25% by weight.

Advantageously, the composition can comprise the non-silicone oil of the oily medium in a content ranging from 2% to 99.9% by weight, with respect to the total weight of the composition, preferably ranging from 5% to 90% by weight, preferably ranging from 10% to 80% by weight, preferably ranging from 20% to 80% by weight.

The copolymer can be obtained in a known way by biosynthesis, for example with the microorganisms belonging to the genus *Pseudomonas*, such as *Pseudomonas resinovorans*, *Pseudomomonas putida*, *Pseudomonas fluorescens*, *Pseudomonas aeruginosa*, *Pseudomonas citronellolis*, *Pseudomonas mendocina*, *Pseudomonas chlororaphis* and preferably *Pseudomonas putida*; and with a carbon source which can be a $C_2$-$C_{20}$, preferably $C_6$-$C_{18}$, carboxylic acid, such as acetic acid, propionic acid, butyric acid, hexanoic acid, heptanoic acid, octanoic acid, nonanoic acid, dodecanoic acid; a saccharide, such as fructose, maltose, lactose, xylose, arabinose, and the like); an n-alkane, such as hexane, octane or dodecane; an n-alcohol, such as methanol, ethanol, octanol or glycerol; methane or carbon dioxide.

The biosynthesis can optionally be carried out in the presence of an inhibitor of the β-oxidation pathway, such as acrylic acid, methacrylic acid, propionic acid, cinnamic acid, salicylic acid, pentenoic acid, 2-butynoic acid, 2-octynoic acid or phenylpropionic acid, and preferably acrylic acid.

Nutrients, such as water-soluble salts based on nitrogen, phosphorus, sulfur, magnesium, sodium, potassium and iron, can also be used for the biosynthesis.

The appropriate known conditions of temperature, pH and dissolved oxygen (DO) can be used for the culturing of the microorganisms.

The microorganisms can be cultured according to any known method of culturing, such as in an unfed or fed mode, batch, continuous mode bioreactor.

The biosynthesis of the polymers used according to the invention is described in particular in the paper "Biosynthesis and Properties of Medium-Chain-Length Polyhydroxyalkanoates with Enriched Content of the Dominant Monomer", Xun Juan et al., Biomacromolecules, 2012, 13, 2926-2932, and in the application WO2011/069244.

The oily medium of the composition according to the invention comprises a non-silicone oil as described above.

The term "oil" is understood to mean a water-immiscible non-aqueous compound which is liquid at ambient temperature (25° C.) and atmospheric pressure (760 mmHg).

The term "hydrocarbon oil" is understood to mean an oil consisting of carbon and hydrogen atoms.

The hydrocarbon oil having from 8 to 16 carbon atoms can be chosen from:
- branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane, isohexadecane and, for example, the oils sold under the Isopar or Permethyl trade names,
- linear $C_8$-$C_{16}$ alkanes, such as n-dodecane ($C_{12}$) and n-tetradecane ($C_{14}$), sold by Sasol respectively under the references Parafol 12-97 and Parafol 14-97, and also their mixtures, the undecane/tridecane mixture, the mixtures of n-undecane ($C_{11}$) and of n-tridecane ($C_{13}$) which are obtained in examples 1 and 2 of the application WO 2008/155059 of Cognis, and their mixtures.

The term "ester oil" is understood to mean an oily compound having one or more ester groups in its chemical structure.

The ester oil can be chosen from:
- oils of vegetable origin, such as triglycerides consisting of fatty acid esters of glycerol in which the fatty acids can have varied chain lengths from $C_4$ to $C_{24}$, it being possible for the latter to be saturated or unsaturated and linear or branched; these oils are in particular triglycerides of heptanoic acid or octanoic acid. The oils of vegetable origin can be chosen from wheat germ, sunflower, grape seed, sesame, peanut, corn, apricot, castor, shea, avocado, olive, soybean, sweet almond, palm, rapeseed, cottonseed, coconut, hazelnut, walnut, rice, linseed, macadamia, alfalfa, poppy, pumpkinseed, sesame, squash, rapeseed, blackcurrant, evening primrose, millet, barley, *quinoa*, rye, safflower, candlenut, passionflower, muscat rose or argan oil; shea butter; or also triglycerides of caprylic/capric acids, such as those sold by Stéarineries Dubois or those sold under the names Miglyol 810®, 812® and 818® by Dynamit Nobel,
- monoester oils of formula $R_4COOR_5$ in which $R_4$ represents a hydrocarbon chain comprising from 5 to 19 carbon atoms and $R_5$ represents a hydrocarbon chain, in particular a branched hydrocarbon chain, containing from 4 to 20 carbon atoms, provided that $R_4+R_5$ is ≥9 carbon atoms and preferably <29 carbon atoms, such as, for example, cetearyl octanoate (PurCellin oil), isopropyl myristate, isopropyl palmitate, hexyl laurate, isononyl isononanoate, 2-ethylhexyl palmitate, isostearyl isostearate, 2-hexyldecyl laurate, 2-octyldecyl palmitate, 2-octyldodecyl myristate, 2-ethylhexyl hexanoate, isononyl hexanoate, neopentyl hexanoate, caprylyl heptanoate or octyl octanoate,
- esters of lactic acid and of $C_{10-20}$ alcohol, such as isostearyl lactate, 2-octyldodecyl lactate, myristyl lactate, $C_{12}$-$C_{13}$ alkyl lactate (Cosmacol® Eli from Sasol), cetyl lactate or lauryl lactate,
- diesters of malic acid and of $C_{10}$-$C_{20}$ alcohol, such as diisostearyl malate, di($C_{12}$-$C_{13}$ alkyl) malate (Cosmacol® EMI from Sasol), dibutyloctyl malate, diethylhexyl malate or dioctyldodecyl malate,
- esters of pentaerythritol and of $C_8$-$C_{22}$ carboxylic acid (in particular tetraesters or diesters), such as pentaerythrityl tetraoctanoate, pentaerythrityl tetraisostearate, pentaerythrityl tetrabehenate, pentaerythrityl tetracaprylate/tetracaprate, pentaerythrityl tetracocoate, pentaerythrityl tetraethylhexanoate, pentaerythrityl tetraisononanoate, pentaerythrityl tetrastearate, pentaerythrityl tetraisostearate, pentaerythrityl tetralaurate, pentaerythrityl tetramyristate, pentaerythrityl tetraoleate or pentaerythrityl distearate;
- diesters of following formula (II) R6-O—C(=O)—R'6-C(=O)—O—R"6, with R6 and R'6, which are identical or different, represent a saturated or unsaturated (preferably saturated) and linear or branched $C_4$ to $C_{12}$ and preferably $C_5$ to $C_{10}$ alkyl chain optionally exhibiting at least one saturated or unsaturated, preferably saturated, ring, and R'6 represents a saturated or unsaturated $C_1$ to $C_4$, preferably $C_2$ to $C_4$, alkylene chain, such as, for example, an alkylene chain derived from succinate (in this case R'6 is a saturated $C_2$ alkylene chain), maleate (in this case R'6 is an unsaturated $C_2$ alkylene chain), glutarate (in this case R'6 is a saturated $C_3$ alkylene chain) or adipate (in this case R'6 is a saturated $C_4$ alkylene chain); in particular, R6 and R"6 are chosen from isobutyl, pentyl, neopentyl, hexyl, heptyl, neoheptyl, 2-ethylhexyl, octyl, nonyl and isononyl; mention may preferentially be made of dicaprylyl maleate or di(2-ethylhexyl) succinate;

diesters of following formula (III) R7-C(=O)—O—R'7-O—C(=O)—R"7, with R7 and R"7, which are identical or different, represent a $C_4$ to $C_{12}$ alkyl chain represent a saturated or unsaturated (preferably saturated) and linear or branched $C_4$ to $C_{12}$ and preferentially $C_5$ to $C_{10}$ alkyl chain, and R'7 represents a saturated or unsaturated $C_1$ to $C_4$, preferably $C_2$ to $C_4$, alkylene chain. Mention may in particular be made of 1,3-propanediol dicaprylate (R7 as $C_7$ and R'7 as $C_3$), sold under the name Dub Zenoat by Stéarinierie Dubois, or dipropylene glycol dicaprylate;

carbonate oils which can be chosen from the carbonates of formula R8-O—CO—O—R9, with R8 and R9, which are identical or different, represent a linear or branched $C_4$ to $C_{12}$ and preferentially $C_6$ to $C_{10}$ alkyl chain; the carbonate oils can be dicaprylyl carbonate (or dioctyl carbonate), sold under the name Cetiol CC® by BASF, di(2-ethylhexyl) carbonate, sold under the name Tegosoft DEC® by Evonik, dipropylheptyl carbonate (Cetiol 4 All from BASF), dibutyl carbonate, dineopentyl carbonate, dipentyl carbonate, dineoheptyl carbonate, diheptyl carbonate, diisononyl carbonate or dinonyl carbonate and preferably dioctyl carbonate.

As described above, the oily medium can comprise a monoalcohol of 2 to 6 carbon atoms. This monoalcohol can be chosen from ethanol, propanol, butanol, pentanol or hexanol. Preferably, the monoalcohol is ethanol or 1-butanol and preferentially ethanol.

Advantageously, the composition according to the invention comprises a physiologically acceptable medium. In particular, the composition is a cosmetic composition.

The term "physiologically acceptable medium" is understood to mean a medium which is compatible with human keratinous substances, such as, for example, the skin, the lips, the nails, the eyelashes, the eyebrows or the hair.

The term "cosmetic composition" is understood to mean a composition which is compatible with keratinous substances, which exhibits a pleasant color, odor and feel, and which does not generate unacceptable discomfort (tingling, tightness, redness) liable to dissuade the consumer from using it.

The term "keratinous substances" is understood to mean the skin (body, face, outline of the eyes, scalp), head hair, eyelashes, eyebrows, body hairs, nails or lips.

The composition according to the invention can comprise a cosmetic additive chosen from water, fragrances, preservatives, fillers, colorants, UV screening agents, oils, waxes, surfactants, moisturizers, vitamins, ceramides, antioxidants, agents for combating free radicals, polymers and thickeners.

Advantageously, the composition according to the invention is a makeup composition, in particular a lip makeup composition, a mascara, an eyeliner, an eye shadow or a foundation.

The composition according to the invention can be in the form of an anhydrous composition, a water-in-oil emulsion or an oil-in-water emulsion.

The term "anhydrous composition" is understood to mean a composition containing less than 2% by weight of water, indeed even less than 0.5% of water and in particular devoid of water. If appropriate, such small amounts of water can in particular be introduced by ingredients of the composition which may contain residual amounts of it.

The invention is illustrated in more detail in the following examples. The amounts are expressed as percentage by weight.

EXAMPLES

Example 1

A polymer was prepared using the *Pseudomonas putida* KT2440 ATCC® 47054™ microorganism and octanoic acid.

The culturing method was carried out under batch axenic conditions in 5 l Fernbach flasks (Corning® ref. 431685) containing 2 l of culture medium, shaken at 110 rev/min at 30° C. in an orbital incubator (diameter of the orbit of 2.5 cm).

The synthesis process was carried out using two distinct culture media. The first culture medium, defined CM1 "inoculum", was used for the preparation of the inoculum. The second culture medium, defined CM2 "batch", was used for unfed batch growth of the microorganism with octanoic acid in the Fernbach flasks.

The composition in grams per liter of the two media is described in the table below:

|  | CM1 "inoculum" | CM2 "batch" |
|---|---|---|
| $(NH_4)_2SO_4$ | 4.7 | 5.02 |
| $Na_2HPO_4 \cdot 7H_2O$ | 12 | 2.24 |
| $KH_2PO_4$ | 2.7 | 0.5 |
| Glucose | 9 | 3.9 |
| $MgSO_4 \cdot 7H_2O$ | 0.8 | 1.03 |
| Citric acid | 1.6 | 1.03 |
| Nutrient Broth (1) | 1 | / |
| Octanoic acid | / | 3.8 |
| Solution Microelements (2) | / | 1.4 |
| 2N NaOH | q.s. for pH = 6.8 | |
| Water | q.s. for 1000 g | |

(1) The composition of the Nutrient Broth, as percentage by weight, is 37.5% beef extract and 62.5% peptone. Reference 233000 DIFCO ™.
(2) The composition of the solution of microelements in grams per liter is described in the table below:

| $FeSO_4 \cdot 7H_2O$ | 10.0 g |
|---|---|
| $CaCl_2 \cdot 2H_2O$ | 3.0 g |
| $ZnSO_4 \cdot 7H_2O$ | 2.2 g |
| $MnSO_4 \cdot 4H_2O$ | 0.5 g |
| $H_3BO_3$ | 0 3 g |
| $CoCl_2 \cdot 6H_2O$ | 0.2 g |
| $Na_2MoO_4 \cdot 2H_2O$ | 0.15 g |
| $NiCl_2 \cdot 6H_2O$ | 0.02 g |
| $CuSO_4 \cdot 5H_2O$ | 1.00 g |
| 0.5N HCl | q.s. for 1000 g |

100 ml of inoculum were prepared by suspending a cryotube containing 1 ml of the strain with 100 ml of "inoculum" culture medium at a pH adjusted to 6.8 with 2N NaOH in a 250 ml Fernbach flask and then incubated at 30° C. at 150 rev/min for 24 h. 1.9 l of CM2 culture medium "BATCH" placed in a presterilized 5 l Fernbach flask were inoculated at OD=0.1 with 100 ml of inoculum. After 70 hours at 30° C. at 110 rev/min, the biomass was dried by lyophilization before being extracted with dichloromethane for 24 h. The suspension was clarified by filtration on a GF/A filter (Whatman®). The filtrate, containing the copolymer in solution in the dichloromethane, was concentrated by evaporation and then dried under high vacuum at 40° C. to constant weight. The crude polyhydroxyalkanoate was purified by precipitation of a solution of the latter in solution in 10 times its weight of dichloromethane from 10 volumes of the solution of cold methanol. The solid obtained was dried under high vacuum at 40° C. to constant weight.

The molecular weight of the polyhydroxyalkanoate obtained was characterized by size exclusion chromatography, refractive index detection.
Eluent: THF
Analytical flow: 1 ml/min
Injection: 100 μl
Columns: 1 Agilent PLGel Mixed-D column 5 μm; 300×7.5 mm; 1 Agilent PLGel Mixed-C column 5 μm; 300×7.5 mm; 1 Agilent Oligopore column; 300×7.5 mm
at ambient temperature (25° C.)
Detection: Waters 2487 Dual I Absorbance Detector, Waters 2414 Refractive Index Detector
Integrator: refractive index at 45° C. and 64 mV
Empower (GPC Module Relative/conventional molar mass)
Injection time Empower 40 min
Standards: High-weight polystyrene/EasiVial PS—H 4 ml from Agilent Technology Part No. PL2010-0200

The analysis makes it possible to measure the weight-average molecular weight (Mw in g/mol), the number-average molecular weight (Mn in g/mol), the polydispersity index PI (Mw/Mn) and the degree of polymerization DPn.

The monomeric composition of the polyhydroxyalkanoate obtained was defined by gas chromatography equipped with a flame ionization detector.

The identification is carried out via the injection of commercial standards and the monomeric composition was determined by methanolysis and silylation treatment.

In order to determine the monomeric composition, 7 mg of the polyhydroxyalkanoate polymer were dissolved in 1.5 ml of chloroform and were methanolyzed in the presence of 1.5 ml of a MeOH/HCl (17/2, v/v) solution at 100° C. for 4 h. The organic phase was subsequently washed with 1 ml of water and then dried over $MgSO_4$. The silylation of the methyl esters formed was carried out by adding 100 μl of BSTFA (N,O-bis(trimethylsilyl)trifluoroacetamide) and 100 μl of pyridine to the methylated sample. The solution was heated at 70° C. for 1 h and then evaporated to dryness. The sample was then dissolved in 600 μl of dichloromethane and analyzed by chromatography under the following conditions:
Hewlett Packard 6890 Series appliance
Stationary phase column ZB-5 HT from Phenomenex (length: 30 m, diameter: 0.25 mm)
Temperature: isothermal 60° C. to 300° C. in 6 min (heating rate: 10° C./min)
Gas: Helium; flow rate: 0.8 ml/min
Injector: Temperature: 250° C.; 50 ml/min
Flame ionization detector; Temperature: 300° C.
Injection: Volume 1 μl A copolymer containing 91% by weight of poly(3-hydroxyoctanoate), 6% by weight of poly(3-hydroxyhexanoate) and 3% by weight of poly(3-hydroxybutanoate) was thus obtained.
Mn=68 100 g/mol
Mw=149 100 g/mol
PI=2.2
DPn=531

Example 2

A polymer was prepared using the *Pseudomonas putida* KT2440 ATCC® 47054™ microorganism, octanoic acid and acrylic acid.

The culturing method was carried out under continuous axenic conditions at a dilution of D=0.25 $h^{-1}$ in a 3 l chemostat containing 1.1 l of culture medium. The system was aerated with air at a flow rate of 3 vvm (vvm=volume of air per volume of fermentation medium per minute) for a dissolved oxygen (DO) setpoint at 30% saturation.

The procurement process was carried out using three distinct culture media. The first undefined culture medium (CM1) was used for the preparation of the inoculum. The second defined culture medium (CM2) was used for the unfed batch growth of the microorganism in the fermenter. The third defined culture medium (CM3) was used for the feeding, or maintenance, of the continuous fermentation containing octanoic acid and acrylic acid (inhibitor of the β-oxidation pathway).

The CM1 and CM2 media are identical to those described in example 1. The composition in grams per liter of the CM3 medium is described in the table below:

|  | CM3 "cotinuous" |
|---|---|
| $(NH_4)_2SO_4$ | 5.02 |
| $Na_2HPO_4 \cdot 7H_2O$ | 2.24 |
| $KH_2PO_4$ | 0.5 |
| Glucose | 3 |
| $MgSO_4 \cdot 7H_2O$ | 1.03 |
| Citric acid | 1.03 |
| Nutrient Broth (1) | / |
| Octanoic acid | 3.8 |
| Solution Microelements (2) | 1.4 |
| Acrylic acid | 0.2 |
| 2N NaOH | q.s. for pH = 6.8 |
| Water | q.s. for 1000 g |

100 ml of inoculum were prepared by suspending a cryotube containing 1 ml of the strain with 100 ml of Nutrient Broth at a pH adjusted to 7.0 with 2N NaOH in a 250 ml Fernbach flask and were then incubated at 30° C. at 150 rev/min for 24 h.

The fermenter containing 1 liter of CM2 culture medium at 30° C. was inoculated at an optical density of 0.1 at 630 nm ($OD_{630}$=0.1). The system was maintained at 30° C. with stirring of 700+/−200 rev/min and adjusted in cascade with oxygenation for approximately 16 h and/or the time that the microorganism can reach its growth plateau.

Feeding the fermenter with the CM3 medium was initiated when the microorganism reached its growth plateau and withdrawal was carried out in order to retain the initial weight of fermentation medium. Once the equilibrium state was reached in continuous culture, a fraction of the withdrawn material was centrifuged in order to separate the biomass from the fermentation medium. The biomass was dried by lyophilization and then extracted with dichloromethane for 24 h. The suspension obtained was clarified by filtration on a GF/A filter (Whatman®). The filtrate obtained, comprising the copolymer in solution in the dichloromethane, was concentrated by evaporation and then dried under high vacuum at 40° C. to constant weight. The crude polyhydroxyalkanoate was purified by precipitation of a solution of the latter in solution in 10 times its weight of dichloromethane from 10 volumes of the solution of cold methanol. The solid obtained was dried under high vacuum at 40° C. to constant weight.

A copolymer comprising 96% by weight of poly(3-hydroxyoctanoate), 3% by weight of poly(3-hydroxyhexanoate) and 1% by weight of poly(3-hydroxybutanoate) was thus obtained.

Mn=67 900 g/mol
Mw=142 000 g/mol
PI=2.1
DPn=611

Example 3

A polymer was prepared according to the procedure of example 2 using nonanoic acid (instead of octanoic acid).

A copolymer comprising 86% by weight of poly(3-hydroxynonanoate), 9% by weight of poly(3-hydroxyheptanoate) and 5% by weight of poly(3-hydroxypentanoate) was thus obtained.

Mn=65 900 g/mol
Mw=143 600 g/mol
PI=2.2
DPn=531

Example 4

A polymer was prepared according to the procedure of example 2 using nonanoic acid (instead of octanoic acid) and without acrylic acid.

A copolymer comprising 68% by weight of poly(3-hydroxynonanoate), 27% by weight of poly(3-hydroxyheptanoate) and 5% by weight of poly(3-hydroxypentanoate) was thus obtained.

Mn=55 800 g/mol
Mw=124 500 g/mol
PI=2.2
DPn=469

Example 5

A polymer was prepared according to the procedure of example 2 using dodecanoic acid (instead of octanoic acid).

A copolymer comprising 44% by weight of poly(3-hydroxydodecanoate), 38% by weight of poly(3-hydroxydecanoate) and 18% by weight of poly(3-hydroxyoctanoate) was obtained.

Mn=67 400 g/mol
Mw=129 800 g/mol
PI=1.9
DPn=484

Example 6 (Outside the Invention)

A copolymer was prepared using the *Pseudomonas resinovorans* ATCC® 14235™ microorganism, hexanoic acid and acrylic acid according to the procedure of example 2.

The composition of the solution of microelements which is used, in grams per liter, is described in the table below:

| | |
|---|---|
| $ZnSO_4 \cdot 7H_2O$ | 0.1 g |
| $MnCl_2 \cdot H_2O$ | 0.03 g |
| $H_3BO_3$ | 0.3 g |
| $CoCl_2 \cdot 6H_2O$ | 0.2 g |
| $Na_2MoO_4 \cdot 2H_2O$ | 0.03 g |
| $NiCl_2 \cdot 6H_2O$ | 0.02 g |
| $CuSO_4 \cdot 5H_2O$ | 0.01 g |
| 0.5N HCl | q.s. for 1000 g |

A copolymer comprising 95% by weight of poly(3-hydroxyhexanoate) and 5% by weight of poly(3-hydroxyoctanoate) was thus obtained.

Mn=107 200 g/mol
Mw=219 100 g/mol
PI=2
DPn=1227

Example 7 (Outside the Invention)

A polymer was prepared according to the procedure of example 2 using heptanoic acid (instead of octanoic acid).

A copolymer comprising 96% by weight of poly(3-hydroxyheptanoate) and 4% by weight of poly(3-hydroxypentanoate) was thus obtained.

Mn=83 600 g/mol
Mw=184 200 g/mol
PI=2.2
DPn=845

Example 8: Test of Solubility in Oils

The solubility in various oils, which are described in the table below, of the polymers of examples 1 to 7, as well as 3 commercial polymers A to C described below, was evaluated.

1 g of polymer was introduced into 9 g of oil in a flask, the mixture was heated at 70° C. with stirring for 1 h, the flask was then placed at ambient temperature for 24 h and the solubility of the polymer in the mixture was observed with the naked eye.

The test was also carried out with 3 commercial polymers outside the invention:

Polymer A: poly(3-hydroxybutanoate), sold under the reference 363502 Aldrich by Sigma-Aldrich Polymer B: poly(3-hydroxybutanoate)-co-(3-hydroxyvalerate), the 3-hydroxyvalerate unit being present at 12 mol %, sold under the reference 403121 Aldrich by Sigma-Aldrich Polymer C: poly(3-hydroxybutanoate)-co-(3-hydroxyvalerate), the 3-hydroxyvalerate unit being present at 8 mol %, sold under the reference 403105 Aldrich by Sigma-Aldrich The following results were obtained:

| | Ex 1 | Ex 2 | Ex 3 | Ex 4 | Ex 5 | Ex 6 | Ex 7 | A | B | C |
|---|---|---|---|---|---|---|---|---|---|---|
| Isododecane | − | − | + | + | + | − | − | − | − | − |
| Isododecane/ethanol 97/3 | + | + | + | + | + | − | − | − | − | − |
| Cetiol UT | − | − | + | | + | | | | | |
| Dodecane | − | − | + | | + | | | | | |

-continued

|   | Ex 1 | Ex 2 | Ex 3 | Ex 4 | Ex 5 | Ex 6 | Ex 7 | A | B | C |
|---|------|------|------|------|------|------|------|---|---|---|
| Parleam | − | − | − | − | + | − | − | − | − | − |
| Parleam/ ethanol 97/3 | − | − | − | − | + | − | − | − | − | − |
| isononyl isononanoate | + | + | + | + | + | − | − | − | − | − |
| Olive oil | + | + | + | + | + | − | − | − | − | − |
| Camelina oil | + | | | | | | | | | |
| Dicaprylyl carbonate | + | | | | | | | | | |
| Silicone L5 | − | − | − | − | − | − | − | − | − | − |

Cetiol UT: undecane/tridecane mixture from BASF
Parleam: hydrogenated polyisobutene from NOF Corporation
Silicone L5: dodecamethylpentasiloxane
+ means that the polymer is soluble in the oil tested: the mixture is homogeneous, clear and stable for one month at ambient temperature
− means that the polymer is not soluble in the oil tested: the mixture is not homogeneous and the polymer precipitates or else the mixture is cloudy The solubility test for the polymer of example 2 was supplemented with other oils described in the table below. The following results were obtained:

|   | Ex 2 |
|---|------|
| squalane | − |
| $C_{15}$-$C_{19}$ Alkane | − |
| Octyldodecanol | − |
| Isododecane/butan-1-ol 97/3 | + |

Example 11: Evaluation of the Film-Forming and Cosmetic Properties

A solution of polymer (polymer of the examples at 10% by weight in isododecane) to be evaluated was deposited on a contrast chart (for example that sold under the reference byko-charts by BYK-Gardner) with a film drawer (speed: 50 mm/s-wet deposit 100 μm thick) and the deposited film was dried for 24 hours at ambient temperature (25° C.). The dry film has a thickness of approximately 10 μm.

The gloss of the film was measured using a glossmeter (three angles Refo 3/Refo 3D from De Lange, Labomat distributor) on the black part of the contrast chart at an angle of 20°.

The resistance of the film obtained was evaluated by separately depositing, on the dry film, two drops (one drop=10 μl) of olive oil and two drops of sebum on the black part of the contrast chart. The drops were left in contact with the dry film for 5 minutes and 30 minutes respectively and subsequently the drop of oil was wiped off and the appearance of the region of the film which was in contact with the oil was observed. If the film was damaged by the drop deposited, the polymer film is regarded is being non-resistant to olive oil and/or to sebum.

The tacky aspect of the polymer film was evaluated by touching the dry film with a finger. The following results were obtained:

| Property | Polymer Example 1 | Polymer Example 2 | Polymer Example 3 | Polymer Example 4 | Polymer Example 5 |
|---|---|---|---|---|---|
| Resistance to Olive oil | Good resistance | Good resistance | Good resistance | Good resistance | Good resistance |
| Resistance to sebum | Good resistance | Good resistance | Good resistance | Good resistance | Good resistance |
| Gloss | Matt film | Matt film | Matt film | Matt film | Matt film |
| Tacky | Non-tacky | Non-tacky | Non-tacky | Non-tacky | Non-tacky |

The results obtained show that the five polymers according to the invention are film-forming and the film obtained is non-tacky, is matt in appearance and exhibits good resistance to oil and to sebum.

Example 12: Cosmetic Evaluation of Makeup Compositions

A makeup composition (lipstick) described below was prepared:

| | |
|---|---|
| Polymer of the invention | 20% |
| Pigment paste comprising 40% by weight of pigment DC Red 7 in isododecane | 5% |
| Isododecane | q.s. for 100% |

The composition was prepared with each polymer of examples 1 to 5.

Each composition was applied on a skin equivalent support made of elastomer by producing a deposited layer with a wet thickness of 100 μm, which was left to dry at ambient temperature (25° C.) for 24 hours.

The resistance of the film obtained was evaluated by separately applying 0.5 ml of olive oil and 0.5 ml of sebum; after 5 minutes of contact, the surface of the film was rubbed with a cotton swab, 25 passes of the cotton swab over the surface being carried out, and then the state of the film was observed (degraded or undegraded appearance of the film).

The resistance of the film to Scotch tape was also evaluated:

A piece of Scotch tape (Scotch® Magic™ 810 from 3M; w=19 mm, l=5 cm) was applied to the dry film. A weight of approximately 1070 g (with a surface area of 65*55 mm) was placed on the piece of Scotch tape for 30 seconds. The Scotch tape was subsequently removed and subsequently deposited on a microscope slide in order to observe the adherent surface of the Scotch tape applied and to see if it contains traces of the dry polymer film. The following results were obtained:

| Property | Polymer Example 1 | Polymer Example 2 | Polymer Example 3 | Polymer Example 4 | Polymer Example 5 |
|---|---|---|---|---|---|
| Resistance to olive oil | Good resistance | Good resistance | Good resistance | Good resistance | Good resistance |
| Resistance to sebum | Good resistance | Good resistance | Good resistance | Good resistance | Good resistance |
| Scotch tape test | Good resistance | Good resistance | Good resistance | Good resistance | Good resistance |

The results obtained show that the compositions according to the invention exhibit good resistance to oil and to sebum and a good persistence (resistance to Scotch tape).

The lipstick composition applied to the lips thus makes it possible to obtain makeup which is resistant to oil and to sebum, thus exhibiting a good persistence.

The invention claimed is:

1. A composition comprising:
   a) a film-forming polyhydroxyalkanoate copolymer comprising the following polymeric units A, B and C:

—[—O—CH(R1)-CH$_2$—CO—]— unit A

—[—O—CH(R2)-CH$_2$—CO—]— unit B

—[—O—CH(R3)-CH$_2$—CO—]— unit C in which:
   R1 denotes a linear alkyl radical having from 5 to 9 carbon atoms;
   R2 denotes a linear alkyl radical having a carbon number corresponding to the number of carbon atoms of the R1 radical −2;
   R3 denotes a linear alkyl radical having a carbon number corresponding to the number of carbon atoms of the R1 radical −4;
   the molar percentage of unit A being greater than the molar percentage of unit B and greater than the molar percentage of unit C; and wherein the unit A is present in a molar percentage ranging from 40% to 97.5%, the unit B is present in a molar percentage ranging from 2% to 40% and the unit C is present in a molar percentage ranging from 0.5% to 20%, with respect to all of the units A, B and C; and
   b) an oily medium comprising a non-silicone oil chosen from:
   ester oils, carbonate oils,
   branched nonpolar hydrocarbon oils having from 8 to 14 carbon atoms, as a mixture with a monoalcohol having from 2 to 6 carbon atoms according to a monoalcohol/branched nonpolar hydrocarbon oil ratio by weight ranging from 1/99 to 10/90; and
   when the polymer is such that the R1 alkyl group has from 6 to 9 carbon atoms, the non-silicone oil is also chosen from nonpolar hydrocarbon oils having from 8 to 14 carbon atoms in the absence of monoalcohol having from 2 to 6 carbon atoms;
   when the polymer is such that the R1 alkyl group comprises 9 carbon atoms, the non-silicone oil is also chosen from hydrogenated polyisobutylenes.

2. The composition as claimed in claim 1, wherein the copolymer comprises units A having an R1 alkyl radical having 5 carbon atoms, units B having an alkyl radical having 3 carbon atoms and units C having an alkyl radical having 1 carbon atom.

3. The composition as claimed in claim 1, wherein the copolymer comprises from 85 mol % to 97.5 mol % of unit A, from 2 mol % to 10 mol % of unit B and from 0.5 mol % to 7 mol % of unit C.

4. The composition as claimed in claim 1, wherein the copolymer comprises units A having an R1 alkyl radical having 6 carbon atoms, units B having an alkyl radical having 4 carbon atoms and units C having an alkyl radical having 2 carbon atoms.

5. The composition as claimed in claim 1, wherein the copolymer comprises from 60 mol % to 94.5 mol % of unit A, from 5 mol % to 35 mol % of unit B and from 0.5 mol % to 7 mol % of unit C.

6. The composition as claimed in claim 1, wherein the copolymer comprises units A having an R1 alkyl radical comprising 9 carbon atoms, units B having an alkyl radical having 7 carbon atoms and units C having an alkyl radical having 5 carbon atoms.

7. The composition as claimed in claim 1, wherein the copolymer comprises from 40 mol % to 50 mol % of unit A, from 30 mol % to 40 mol % of unit B and from 10 mol % to 20 mol % of unit C.

8. The composition as claimed in claim 1, wherein the copolymer has a number-average molecular weight ranging from 50 000 to 150 000.

9. The composition as claimed in claim 1, wherein the copolymer is present in a content ranging from 0.1% to 30% by weight, with respect to the total weight of the composition.

10. The composition as claimed in claim 1, wherein the nonpolar hydrocarbon oil having from 8 to 16 carbon atoms is chosen from branched $C_8$-$C_{16}$ alkanes and linear $C_8$-$C_{16}$ alkanes.

11. The composition as claimed in claim 1, wherein the ester oil is chosen from triglycerides consisting of $C_4$-$C_{24}$ fatty acid esters of glycerol; monoester oils of formula $R_4COOR_5$ in which $R_4$ represents a hydrocarbon chain comprising from 5 to 19 carbon atoms and $R_5$ represents a hydrocarbon chain provided that $R_4+R_5$ is ≥9 carbon atoms; esters of lactic acid and of $C_{10-20}$ alcohol; diesters of malic acid and of $C_{10}$-$C_{20}$ alcohol; esters of pentaerythritol and of $C_8$-$C_{22}$ carboxylic acid; diesters of formula (II) R6-O—C(=O)—R'6-C(=O)—O—R"6, with R6 and R"6, which are identical or different, represent a saturated or unsaturated and linear or branched $C_4$ to $C_{12}$ alkyl chain optionally exhibiting at least one saturated or unsaturated ring, and R'6 represents a saturated or unsaturated $C_1$ to $C_4$ alkylene chain; diesters of formula (III) R7-C(=O)—O—R'7-O—C(=O)—R"7, with R7 and R"7, which are identical or different, represent a $C_4$ to $C_{12}$ alkyl chain represent a saturated or unsaturated and linear or branched $C_4$ to $C_{12}$ alkyl chain, and R'7 represents a saturated or unsaturated $C_1$ to $C_4$ alkylene chain.

12. The composition as claimed in claim 1, wherein the carbonate oils are chosen from the carbonates of formula R8-O—CO—O—R9, with R8 and R9, which are identical or different, represent a $C_4$ to $C_{12}$ alkyl chain.

13. The composition as claimed in claim 1, which comprises a monoalcohol of 2 to 6 carbon atoms.

14. The composition as claimed in claim 1, which it comprises a physiologically acceptable medium.

15. A nontherapeutic cosmetic method for the treatment of keratinous substances, comprising the application, to the keratinous substances, of a composition as claimed in claim 1.

16. The composition as claimed in claim 1 wherein the polyhydroxyalkanoate copolymer consists of the polymeric units A, B and C.

17. The composition as claimed in claim 13 wherein the monoalcohol is chosen from ethanol or 1-butanol.

18. The composition as claimed in claim 13 wherein the monoalcohol is ethanol.

19. The composition as claimed in claim 11, wherein the copolymer comprises units A having an R1 alkyl radical having 5 carbon atoms, units B having an alkyl radical having 3 carbon atoms and units C having an alkyl radical having 1 carbon atom; and wherein the copolymer comprises from 85 mol % to 97.5 mol % of unit A, from 2 mol % to 10 mol % of unit B and from 0.5 mol % to 7 mol % of unit C.

20. The composition as claimed in claim 1, wherein the copolymer comprises units A having an R1 alkyl radical having 6 carbon atoms, units B having an alkyl radical having 4 carbon atoms and units C having an alkyl radical having 2 carbon atoms; wherein the copolymer comprises from 60 mol % to 94.5 mol % of unit A, from 5 mol % to 35 mol % of unit B and from 0.5 mol % to 7 mol % of unit C.

21. The composition as claimed in claim 1, wherein the copolymer comprises units A having an R1 alkyl radical comprising 9 carbon atoms, units B having an alkyl radical having 7 carbon atoms and units C having an alkyl radical having 5 carbon atoms; and wherein the copolymer comprises from 40 mol % to 50 mol % of unit A, from 30 mol % to 40 mol % of unit B and from 10 mol % to 20 mol % of unit C.

* * * * *